United States Patent [19]

Hahn et al.

[11] 4,149,078
[45] Apr. 10, 1979

[54] COUNTERWEIGHT COMPENSATION FOR AN X-RAY EXAMINATION APPARATUS

[75] Inventors: Alfred Hahn, Erlangen; Hans P. Dornheim, Bubenreuth, both of Fed. Rep. of Germany

[73] Assignee: Siemens Aktiengesellschaft, Berlin & Munich, Fed. Rep. of Germany

[21] Appl. No.: 872,604

[22] Filed: Jan. 26, 1978

[30] Foreign Application Priority Data

Feb. 3, 1977 [DE] Fed. Rep. of Germany ....... 2704528

[51] Int. Cl.² .......................................... G01N 21/34
[52] U.S. Cl. ................................. 250/439 R; 250/444
[58] Field of Search ............... 250/439 R, 444, 445 R, 250/445 T, 446, 447, 448, 449, 450; 269/323, 324

[56] References Cited

U.S. PATENT DOCUMENTS 3,916,203 10/1975 Norgren ................................. 250/444
3,933,251 1/1976 Schmedemann ..................... 250/444

Primary Examiner—Craig E. Church
Attorney, Agent, or Firm—Hill, Gross, Simpson, Van Santen, Steadman, Chiara & Simpson

[57] ABSTRACT

In the illustrated embodiment, a single counterweight suspended on a traction cable compensates a plurality of differently moving apparatus parts and is of significantly lesser weight than corresponds to the sum of weights of the compensated apparatus parts. The cable is shown as coupled with the sighting device beneath the patient's support as well as with the carrier column for the X-ray tube while yet being operable to simultaneously compensate the torque of the carrier column in different orientations of the patient support, including a vertical disposition.

3 Claims, 1 Drawing Figure

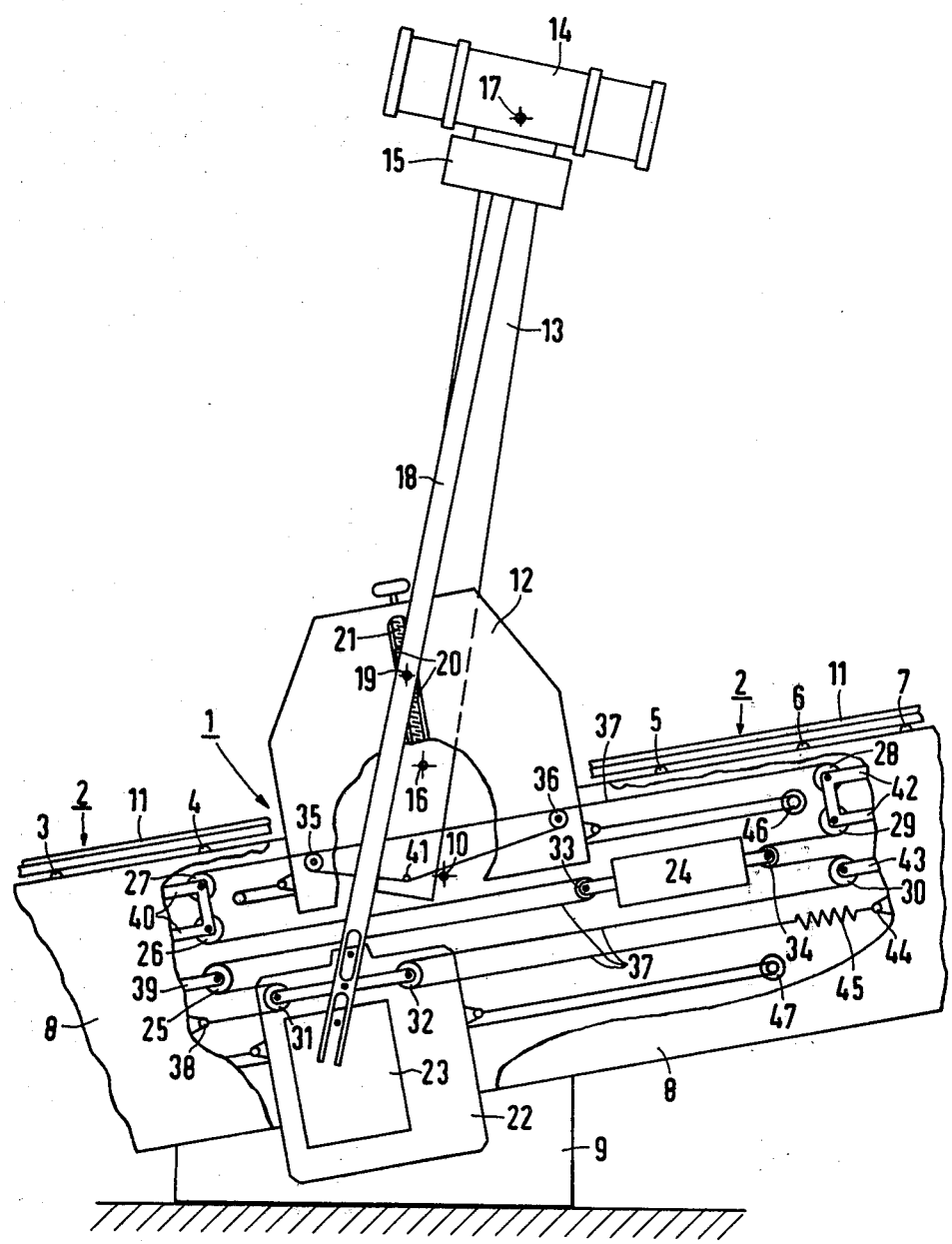

COUNTERWEIGHT COMPENSATION FOR AN X-RAY EXAMINATION APPARATUS

BACKGROUND OF THE INVENTION

The invention relates to a counterweight compensation assembly for an X-ray examination apparatus, comprising a patient support location tiltable about a horizontal axis of tilt, a sighting device displaceable along the length of the patient support, and a carrier column for the X-ray tube which is pivotably mounted about an additional horizontal axis on a pillow block displaceable along the length of the patient support.

In X-ray technology, the compensation of the weight of an apparatus part, whch must be adjusted in its height in accordance with operation, via a counterweight is variously known. This counterweight is then displaceable in a guide path which is aligned parallel to the guide path of the apparatus part which is to be compensated. The countereweight and the apparatus part which is to be compensated are interconnected in such a fashion that they move in precisely opposite directions. In this manner, the weight of the apparatus part to be adjusted is precisely compensated in every tilt position of the X-ray examination apparatus.

Accordingly, in the case of X-ray examination apparatus manifesting a plurality of mutually adjustable apparatus parts, an equal number of counterweight compensation devices are required, independently of one another, each of which is associated with one apparatus part, respectively. The disadvantage connected herewith is that the overall weight of the X-ray examination apparatus is significantly enlarged by the plurality of counterweights which, in the case of a two-dimensional displaceability of the apparatus part, must be compensated again in turn. Due to the required carrying capacity of the floors, this again restricts the use of such apparatus to buildings with floors having a corresponding bearing capacity.

SUMMARY OF THE INVENTION

The object underlying the invention addresses an X-ray examination apparatus of a complicated construction, said object consisting in compensating the weights of the different apparatus parts contained therein, which are displaceable independently of one another, with one single counterweight. As a result, the installed power levels of the motor drives which are to be employed for the displacement of the apparatus parts, as well as the costs of these drives, are to be reduced, or the adjustment of these apparatus parts is to be selectively facilitated by hand.

Accordingly, in the case of a counterweight compensation of the type initially cited, the invention specifies that the weights of the sighting device, the pillow block, the carrier column of the X-ray tube, and the torque of the carrier column be compensated via a single counterweight suspended on a traction cable, whereby the traction cable, proceeding from a fixed point on one side of the essentially parallel displacement paths of the apparatus parts to be compensated, is alternately guided about at the apparatus parts to be compensated, as well as at the counterweight, and at cable pulleys suspended at fixed points, and, in its further course, it is guided on the opposite side of the displacement paths to an additional fixed point via similarly suspended cable pulleys. The significant advantage connected therewith is that the overall weight of the counterweight can be kept smaller, because the latter simultaneously compensates a plurality of apparatus parts, whereby the weight of each of these apparatus parts can be equal to the weight of the counterweight. In addition, as a consequence of suspending the structural components between two free-running traction cables, it has been possible to achieve a random relative displaceability of these structural units with respect to one another.

A particularly expedient method of construction, which is also adapted to the spatial conditions of the X-ray examination apparatus with an upper-table X-ray tube, results if the traction cable—in an advantageous further embodiment of the invention—proceeding from one fixed point on one side of the displacement paths of the apparatus parts to be compensated, is guided in succession about a cable pulley mounted on the sighting device, a cable pulley mounted on a fixed point, a cable pulley mounted on the counterweight, a cable pulley mounted an additional fixed point, and a cable pulley mounted on the pillow block, if said traction cable is mounted onto the end of the carrier column remote from the X-ray tube, and if it is again returned to an additional fixed point with opposite tractive direction, respectively, on the other side of the displacement path of these apparatus parts via cable pulley suspended on the same apparatus parts and on oppositely disposed fixed points. This method of construction makes it possible to arrange the counterweight compensation device in the carrier member of the patient support under the same, and to tension it between the walls of this carrier member. In addition, there is the additional connected advantage that not only the apparatus parts, but the torque of the pivotably mounted carrier column of the X-ray tube are to be simultaneously compensated. It is indeed already known from the German Offenlegungsschrift No. 2,133,633, in the case of a support column of an X-ray examination apparatus, to compensate the weight of the tube-image layer (or film) carrier mounted onto a carrier column, as well as its torque, with one single counterweight coupled in the common center of gravity. However, this would count upon the support of the carrier column in the center of gravity, which is not possible in the case of the guidance of the cable beneath the patient's support for the purpose of also compensating the sighting device disposed therein.

The invention shall be explained in further detail in the following on the basis of a sample embodiment illustrated in a FIGURE on the accompanying sheet of drawings; other objects, features and advantages will be apparent from this detailed disclosure and from the appended claims.

BRIEF DESCRIPTION OF THE DRAWING

The single FIGURE is a somewhat diagrammatic partial side elevational view, with portions broken away to show internal details.

DETAILED DESCRIPTION

In the FIGURE, an X-ray examination apparatus 1 is illustrated with a patient support 2 tilted approximately 30° from the horizontal for purposes of clarity. The patient support 2 is guided in a longitudinally displaceable fashion by means of rollers 3, 4, 5, 6, 7, on a carrier member 8. This carrier member 8, in turn, is mounted onto a pedestal 9 such that it is capable of tilting movement about a horizontal axis 10. The upper side of the patient support 2 is closed off by a patient support plate 11. Laterally of the carrier member 8 and patient support 2, a pillow block 12 is mounted on carrier member 8 such that it is capable of displacement in the longitudinal direction of the patient support 2. Mounted on pillow block 12, in turn, is a carrier column 13 for an X-ray tube 14 and a radiation diaphragm (or collimator) 15 flanged onto the X-ray tube, the aforementioned being mounted such as to be pivotable about a horizontal axis 16 extending parallel to the tilt axis 10 of the carrier member 8. In addition, the X-ray tube 14, together with the radiation diaphragm (or collimator) 15 on the carrier column 13 is rotatable about an axis 17 traversing the focal point. This axis 17 extends parallel to axis 16 about which the carrier column 13 can be pivoted. X-ray tube 14 is rigidly coupled with a planigraphic (or tomographic) rod 18. The tomographic rod 18, in turn, is pivotable about a tomographic rod 19 which is aligned parallel to axis 16 about which the carrier column 13 can be pivoted. This tomographic bar 19 is mounted onto a threaded bolt 20 which is adjustable along a spindle 21 aligned on the pillow block 12 vertically to the plane of the patient support plate 11. At the end of the planigraphic rod 18 which is remote from X-ray tube 14, said rod is coupled together with a sighting device 22 beneath the plane of the patient support plate 11, said sighting device 22 being displaceable in the interior of the carrier member 8 along the patient support, and said planigraphic rod 18 being here also coupled together with an image intensifier 23 displaceable in the sighting device in the same direction.

In carrier member 8, a counterweight 24 is displaceably mounted along guides not illustrated here for purposes of clarity. Cable pulleys 25, 26, 27, 28, 29, 30, are mounted to the end faces of carrier member 8 which are facing the two narrow sides of the patient support 2. In addition, additional cable pulleys 31, 32, 33, 34, 35, 36, are mounted onto the structural units (or components) which are to be adjusted, such as the pillow block 12, counterweight 24, and planigraphic rod 18, these cable pulleys being mounted in the region between the coupling points of the assembly units on the sighting device 22 and image intensifier 23. Proceeding from the one fixed point 38, the traction cable 37 is guided about the cable pulley 31 mounted onto the planigraphic rod 18, and is guided about the cable pulley 25 mounted on the left fixed point 39, about a cable pulley 33 mounted at the left on counterweight 24, and about two cable pulleys 26, 27, mounted on the left fixed point 40, about the right cable pulley 36 of the pillow block 12 to a mounting point 41 on the carrier column 13 of the X-ray tube 14, about the left cable pulley 35 of pillow block 12 to the two cable pulleys 28, 29, mounted on the right fixed point 42, via a right cable pulley 34 of counterweight 24 about the individual right cable pulley 30 mounted to fixed point 43, and via the right cable pulley 32 on the planigraphic rod 18, is conveyed back to the right fixed point 44, which is necessary for the purpose of compensating the weight of the X-ray tube 14 and radiation diaphragm (or collimator) 15, taking into account the different lever arms of carrier column 13 in the case of a vertically positioned patient support 2 and a horizontal carrier column 13, is equal to half the common weight of the sighting device 22 and the image intensifier 23. In order to compensate the cable length, the traction cable 37 is mounted to a fixed point 44 pursuant to the intermediate connection of a tension spring 45. In the opened-up carrier member 8, finally, a motor drive 46 for the displacement of the pillow block 12 and a motor drive 47 for the displacement of the planigraphic rod 18 is apparent.

Under the following conditions, pillow block 12, carrier column 13, sighting device 22, and image intensifier 23 are equilibrated (or weight-counter balanced, or counterweighted) in all tilt positions of the X-ray examination apparatus 1. The weight of the counterweight 24 must be equally as great as the common weights of sighting device 22 and image intensifier 23, on the one hand, and double as great as the weight of pillow block 12, on the other hand. In addition, the weight of the counterweight 24 must correspond approximately to double the tensile force which is required in the instance of a horizontal carrier column 13 and a vertically positioned patient support 2, in order to keep the latter in equilibrium at the mounting point 41 of traction cable 37 on the carrier column. The guidance of the single traction cable 37, via free running cable pulleys 31, 32, 33, 34, 35, 36, mounted onto the planigraphic rod 18, the single counterweight 24, and the pillow block 12, permits the displacement of the pillow block 12 as well as also the sighting device 22 with the image intensifier independently of one another. Basically, it does not matter in which sequence the counterweight, the pillow block, or the sighting device with the image intensifier are secured to the traction cable 37. The guidance of the traction cable illustrated in the FIGURE is particularly expedient only for spatial reasons. Given longitudinal movement in the same direction of pillow block 12, sighting device 22 and image intensifier 23, the counterweight covers 1.5 times the distance in the opposite direction. In the case of tomograms, in which the carrier column 13 and the planigraphic (or tomographic) rods 18 pivot about their axes 16, 19 on the arrested pillow block 12, whereby the image intensifier 23 coupled via planigraphic rod 18 and the sighting device 22 are displaced in a direction opposite to that of the X-ray tube, the counterweight 24 is displaced (or shifted) in opposite direction a lesser distance than the cable pulleys 31, 32 mounted onto the planigraphic rod 18, because the carrier column 13 is jointly pivoted via the planigraphic rod. The minimum amount is dependent upon the pivot angle of the carrier column 13 and thus is dependent upon the height of the planigraphic rod 19 which is adjusted on the spindle 21. Sighting device 22 with image intensifier 23 is illustrated in the figure at an exaggeratedly large distance from the patient support plate 11 only for purposes of clarity.

The particular advantage of this type of counterweight compensation is based on the fact that a plurality of apparatus parts can be compensated with only one single counterweight of significantly lesser weight than corresponds to the sum of the weights of the apparatus parts to be compensated. As a result, the X-ray examination apparatus 1 becomes lighter and simpler than with a plurality of independent counterweights. Through use of this counterweight compensation motor drives 46, 47 can be dimensioned such that they are weaker in power and thus more favorable in cost. The largest drive power for pivoting of the carrier 13 is required in the case of a horizontal patient support and a carrier column 13 which has been pivoted to the maximum extent. Drive 47 is to be dimensioned according to this requirement.

Although we have described our invention by reference to a particular illustrative embodiment thereof, many changes and modifications of the invention may become apparent to those skilled in the art without departing from the spirit and scope of the invention. We therefore intend to include within the patent warranted hereon all such changes and modifications as may reasonably and properly be included within the scope of my contribution to the art.

We claim as our invention:

1. A counterweight compensation system for an X-ray examination apparatus, comprising a patient support tiltable about a horizontal axis, a sighting device which is displaceable along the length of the patient support, and a carrier column for the X-ray tube which is pivotably mounted about an additional horizontal axis on a pillow block displaceable along the length of the patient support, characterized in that the weights of the sighting device (22), the pillow block (12), the carrier column (13) for the X-ray tube (14) and the torque of the carrier column are compensated via a single counterweight (24) suspended on a traction cable (37), such that traction cable, proceeding from a fixed point (38) on one side of the essentially parallel displacement paths of the apparatus parts to be compensated, is alternately guided about cable pulleys (25, 26, 27, 31, 33, 36) suspended on each of the respective apparatus parts to be compensated as well as on the counterweight and on fixed points (39, 40, 42, 43) at each end of the tiltable support, and in its further course, is guided to an additional fixed point (44) on the respective opposite side of the displacement paths via a plurality of similarly suspended cable pulleys (28, 29, 30, 32, 34, 35) along said course.

2. A counterweight compensation system according to claim 1, characterized in that the traction cable (37), proceeding from a fixed point (38) on one side of the displacement paths of the apparatus parts to be compensated, is successively guided about a cable pulley mounted on the sighting device (22), a cable pulley mounted on a fixed point (39), a cable pulley mounted on the counterweight (24) a cable pulley mounted on an additional fixed point (40), and a cable pulley mounted on the pillow block (12), said traction cable being mounted to the end of the carrier column (13) remote from the X-ray tube (14), and, with a respective opposite tractive direction, is again returned to an additional fixed point (44) on the other side of the displacement path of these apparatus parts via cable pulleys (28, 29, 30, 32, 34, 35) suspended on the same apparatus parts and on opposite fixed points (42,43).

3. A counterweight compensation system according to claim 1, characterized in that, pursuant to the utilization of a planigraphic rod (18) orientating the X-ray tube (14) to the sighting device, and an image intensifier (23) displaceable via the planigraphic rod relative to the sighting device in the longitudinal direction of the patient support (2), the cable pulleys (31, 32) associated with the sighting device (22) are coupled to the planigraphic rod at the common center of gravity of the sighting device and the image intensifier.

* * * * *